United States Patent [19]

Model

[11] 4,327,024
[45] Apr. 27, 1982

[54] IMINOISOINDOLINONE PIGMENTS, PROCESS FOR THEIR PRODUCTION AND USE THEREOF

[75] Inventor: Ernst Model, Basel, Switzerland

[73] Assignee: Ciba-Geigy Corporation, Ardsley, N.Y.

[21] Appl. No.: 205,806

[22] Filed: Nov. 10, 1980

[30] Foreign Application Priority Data

Nov. 20, 1979 [CH] Switzerland .................. 10343/79

[51] Int. Cl.$^3$ .................. C07D 209/50; C08K 5/00
[52] U.S. Cl. .................. 260/325 PH; 106/23; 106/288 Q; 524/94
[58] Field of Search .................. 260/325 PH

[56] References Cited

U.S. PATENT DOCUMENTS

| | | | |
|---|---|---|---|
| 2,973,358 | 2/1961 | Pugin | 260/240 |
| 3,787,438 | 1/1974 | Thomas | 260/325 PH |
| 3,816,448 | 6/1974 | Bitterli et al. | 260/325 PH |
| 3,839,356 | 10/1974 | Diana | 260/325 PH |
| 3,849,438 | 11/1974 | Houlihan et al. | 260/325 PH |
| 3,971,805 | 7/1976 | Model | 260/325 PH |
| 4,070,367 | 1/1978 | Model | 260/325 PH |
| 4,223,152 | 9/1980 | Fujii et al. | 260/325 PH |
| 4,231,931 | 11/1980 | Model | 260/325 PH |

*Primary Examiner*—G. T. Breitenstein
*Attorney, Agent, or Firm*—Harry Falber

[57] ABSTRACT

Iminoisoindolinone pigments of the formula

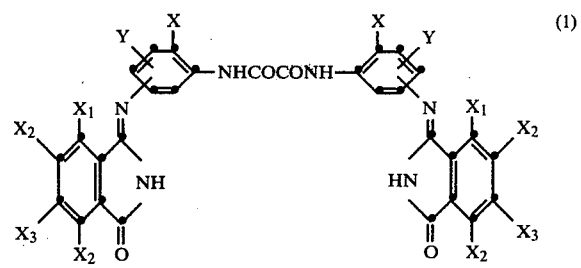

are pigments with excellent color strength and good fastness to light, atmospheric influences, heat and migration, and are suitable for pigmenting organic material of high molecular weight.

4 Claims, No Drawings

IMINOISOINDOLINONE PIGMENTS, PROCESS FOR THEIR PRODUCTION AND USE THEREOF

The present invention relates to valuable novel iminoisoindolinone pigments of the formula

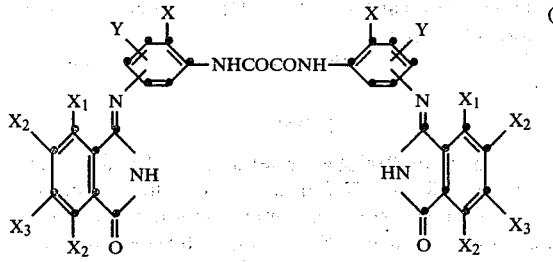
(1)

wherein X and Y are hydrogen, halogen, alkyl or alkoxy, each of 1 to 4 carbon atoms, $X_2$ is chlorine or bromine and $X_1$ and $X_3$ are chlorine, bromine, alkoxy of 1 to 4 carbon atoms, or aryloxy.

Particularly interesting iminoisoindolinone pigments are those of the formula

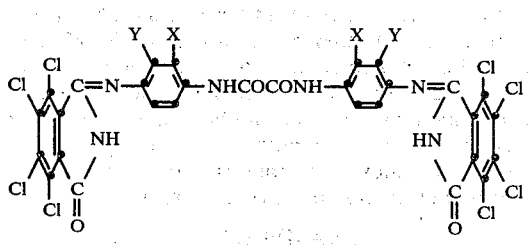
(2)

wherein X is hydrogen or methoxy and, preferably, chlorine or methyl, and Y is hydrogen, methyl or chlorine.

The iminoisoindolinone pigment of the formula

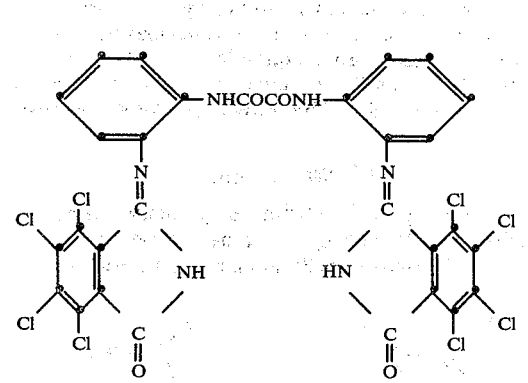
(3)

is also of interest.

The iminoisoindolinone pigments of the formula I are obtained by condensing an isoindolinone of the formula

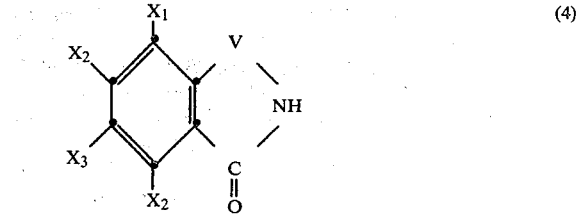
(4)

wherein V is a group of the formula

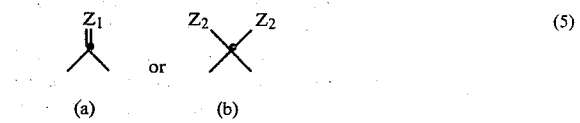
(5)

in which $Z_1$ is an imino or thio group and $Z_2$ is halogen, alkoxy or a secondary amino group, with a diamine of the formula

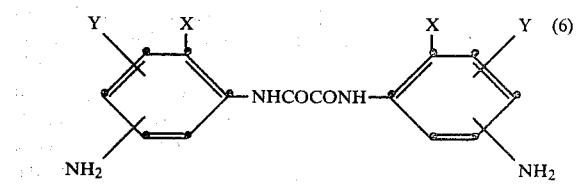
(6)

wherein X and Y are hydrogen, halogen, alkyl or alkoxy, each of 1 to 4 carbon atoms, in the molar ratio 2:1.

The starting materials employed are preferably isoindolinones of the formula

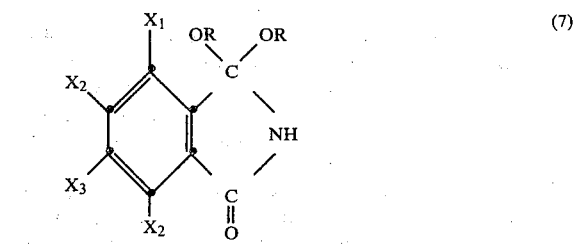
(7)

wherein R is alkyl of 1 to 4 carbon atoms, and $X_1$ to $X_3$ have the given meanings. The preferred starting materials are isoindolinones of the formula (7), wherein $X_1$ to $X_3$ are chlorine or bromine.

Representative examples of starting materials of the formula (7) are:
3-imino-4,5,6,7-tetrachloroisoindolinone
3-imino-5,7-dichloro-4,6-dimethoxyisoindolinone
3,3,4,5,6,7-hexachloroisoindolinone
3,3-dimethoxy-5,7-dichloro-4,6-dimethoxyisoindolinone
3,3-dimethoxy-4,5,7-trichloro-6-methoxyisoindolinone
3,3-dimethoxy-4,5,6,7-tetrachloroisoindolinone
3,3-dimethoxy-4,5,6,7-tetrabromoisoindolinone
3,3-dimethoxy-4,5,7-trichloro-6-n-ethoxyisoindolinone
3,3-dimethoxy-4,5,7-trichloro-6-n-propoxyisoindolinone
3,3-dimethoxy-4,5,7-trichloro-6-butoxyisoindolinone
3,3-dimethoxy-4,5,7-trichloro-6—phenoxyisoindolinone.

The above isoindolinones are known compounds. The condensation of the isoindolinone with the diamine is carried out partly at low temperature, optionally by warming the homogeneously mixed components, preferably in the presence of an inert organic solvent.

Where the starting materials are 3-imino-, 3-thio-or 3,3-bis-sec-amino-4,5,6,7-tetrachloroisoindolin-1-ones or alkali metal salts of 3,3-dialkoxy-4,5,6,7-tetrahaloisoindolin-1-ones, then it is advantageous to use water-miscible organic solvents, e.g. lower aliphatic alcohols such as lower alkanols, e.g. methanol, isopropanol or butanol; lower cyclic ethers such as dioxane, ethylene glycol monomethyl ether; lower aliphatic ketones such as acetone; dimethyl formamide or dimethyl acetamide. In doing so, the condensation is able to take place at relatively low temperatures. It is advantageous to conduct the reaction in the presence of an agent that binds alkali and organic bases, for example a lower fatty acid which can be used simultaneously as solvent, especially acetic acid.

If the starting material is a 3,3,4,5,6,7-hexahaloisoindolin-1-one, it is preferred to use an organic solvent that does not contain hydroxyl groups, for example an aromatic hydrocarbon such as benzene, toluene, xylene, tetrahydronaphthalene or diphenyl; a cycloaliphatic hydrocarbon, for example cyclohexane; a halogenated aliphatic hydrocarbon, for example carbon tetrachloride or tetrachloroethylene, or a halogenated aromatic hydrocarbon, for example chlorobenzene or a dior trichlorobenzene; also a nitrohydrocarbon, for example nitrobenzene; an aliphatic ether, for example dibutyl ether; an aromatic ether, for example diphenyl ether, or a cyclic ether, for example dioxane; also a ketone, for example acetone; or an ester, for example an ester of a lower fatty acid with a lower alkanol, for example ethyl acetate, in the presence of an acid acceptor.

Preferred diamines of the formula (6) are: 4,4'-diamino-oxalyl dianilide, 4,4'-diamino-2,2'-dimethyloxalyl dianilide, 4,4'-diamino-2,2'-dichloro-oxalyl dianilide, 4,4'-diamino-2,2'-dimethoxy-oxalyl dianilide, 4,4'-diamino-2,2'-diethoxy-oxalyl dianilide, and 2,2'-diamino-oxalyl dianilide.

The above amines are known or they can be obtained by known methods, for example by reaction of oxylyl chloride with an unsubstituted or substituted nitroaniline and subsequent reduction.

Directly after their formation, the pigments of the present invention fall out of the reaction mixture. For certain purposes they can be used direct as crude pigments; but their properties, especially with respect to purity, form, and hiding power, can also be improved by known methods, for example by extraction with organic solvents or by grinding with grinding assistants which can afterwards be removed, e.g. salts, or by precipitation with an alkali.

The iminoisoindolinones of this invention are useful pigments which, surprisingly, despite interrupted conjugation in their structural formula, are distinguished by brilliance, high colour strength, excellent purity of shade, and good dispersibility. In addition, they have good fastness to light, atmospheric influences, overspraying, heat and migration. They can be used in finely dispersed form for pigmenting organic material of high molecular weight, e.g. cellulose ethers and esters, such as ethyl cellulose, acetyl cellulose, nitrocellulose, polyamide and polyurethanes, or polyesters, natural resins or synthetic resins, e.g. aminoplasts, especially urea-formaldehyde and melamine-formaldehyde resins, alkyd resins, phenolic plastics, polycarbonates, polyolefins such as polystyrene, polyvinyl chloride, polyethylene, polypropylene, polyacrylonitrile, polyacrylates, thermoplastics or curable acrylic resins, rubber, casein, silicone and silicone resins, singly or in mixtures. It is immaterial whether the specified materials of high molecular weight are in the form of plastics, melts or of spinning solutions, lacquers, paints or printing inks. Depending on the end-use, it is advantageous to use the pigments of the present invention as toners or in the form of preparations.

The invention is illustrated by the following Examples.

EXAMPLE 1

17.25 g of methyl 3,4,5,6-tetrachloro-1-cyanobenzoate are stirred with 57.5 ml of a 1N sodium methylate solution in methanol until a clear solution is obtained. The sodium salt of 3,3-dimethoxy-4,5,6,7-tetrachloroisoindolin-1-one forms. With efficient stirring, 7.5 g of finely ground and sieved oxalyl-bis(4-amino-2-methylanilide), 100 ml of o-dichlorobenzene and 25 ml of dimethyl formamide are then added. At a bath temperature of 130° C., the internal temperature is raised in the course of about 30 minutes to 100° C. while distilling off methanol, whereupon the sodium salt of the pigment precipitates without a clear solution having formed. The batch is diluted with a further 100 ml of o-dichlorobenzene, stirred for 1 hour at 100° C., and then acidified with 20 ml of glacial acetic acid. The temperature is raised to 140°-150° C. and kept for 2 hours. The insoluble pigment is collected by filtration at 120° C. and washed with hot methanol, acetone, and hot water and then dried, affording 20.2 g of a productive yellow pigment which, in this form, can be used for colouring plastics and for the preparation of printing pastes and lacquers. The yellow colourations obtained are distinguished by outstanding fastness properties.

EXAMPLE 2

A yellow pigment with similar properties is obtained by using methyl 3,4,5,6-tetrabromo-o-cyanobenzoate in Example 1 instead of methyl 3,4,5,6-tetrachloro-o-cyanobenzoate.

EXAMPLE 3

A yellow pigment having similarly good properties when incorporated in plastics, printing pastes and lacquers, is obtained by using equimolar amounts of methyl 3,4,6-trichloro-5-methoxy-o-cyanobenzoate in Example 1 instead of methyl 3,4,5,6-tetrachloro-o-cyanobenzoate.

EXAMPLE 4 to 21

The following table lists further pigments which are obtained by condensing 3,3-dimethoxy-4,5-6,7-tetrachloroisoindolin-1-one with a diamine of the formula

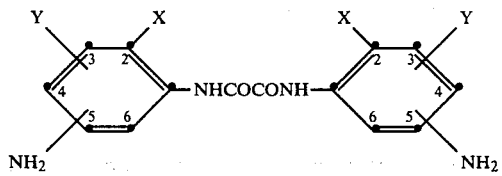

wherein NH₂ and Y are in the positions indicated in the table, and X and Y have the given meanings.

| No. | NH₂ | X | Y | Shade |
|---|---|---|---|---|
| 4 | 2,2' | H | H | yellow |
| 5 | 2,2' | H | 4,4'-Cl | greenish yellow |
| 6 | 2,2' | H | 4,4'-CH₃ | yellow |
| 7 | 3,3' | H | H | greenish yellow |
| 8 | 3,3' | H | 4,4'-CH₃ | greenish yellow |
| 9 | 5,5' | CH₃ | H | greenish yellow |
| 10 | 4,4' | H | H | yellow |
| 11 | 4,4' | OCH₃ | H | yellow |
| 12 | 4,4' | H | 3,3'-CH₃ | yellow |
| 13 | 4,4' | Cl | H | greenish yellow |
| 14 | 4,4' | CH₃ | 5,5'-CH₃ | yellow |
| 15 | 4,4' | CH₃ | 3,3'-CH₃ | yellow |
| 16 | 4,4' | OCH₃ | 5,5'-CH₃ | yellow |
| 17 | 4,4' | CH₃ | 3,3'-Cl | yellow |
| 18 | 4,4' | OCH₃ | 5,5'-OCH₃ | orange |
| 19 | 4,4' | OC₂H₅ | 5,5'-OC₂H₅ | orange |
| 20 | 4,4' | Cl | 3,3'-Cl | greenish yellow |
| 21 | 4,4' | Cl | 5,5'-Cl | greenish yellow |

EXAMPLE 22

2 g of the pigment obtained in Example 10 are ground with 36 g of toner dehydrate, 60 g of boiled linseed oil of medium viscosity and 2 g of cobalt linoleate on a three roll mill. The yellow prints obtained with the resultant colour paste are strong and of excellent lightfastness.

EXAMPLE 23

0.6 g of the pigment obtained in Example 13 is mixed with 67 g of polyvinyl chloride, 33 g of dioctyl phthalate, 2 g of dibutyl tin dilaurate and 2 g of titanium dioxide and the mixture is processed to a thin sheet for 15 minutes at 160° C. on a roll mill. The yellow colouration obtained is strong and fast to migration, heat and light.

EXAMPLE 24

10 g of titanium dioxide and 2 g of the pigment obtained in Example 1 are ground for 48 hours in a ball mill with 88 g of a mixture of 26.4 g of coconut alkyd resin, 24 g of melamine/formaldehyde resin (50% solids content), 8.8 g of ethylene glycol monomethyl ether and 28.8 g of xylene. The resultant lacquer is sprayed onto an aluminium sheet, predried for 30 minutes at room temperature and then stoved for 30 minutes at 120° C. The yellow finish obtained has excellent colour strength and very good fastness to overspraying, light and atmospheric influences.

What is claimed is:

1. An iminoisoindolinone pigment of the formula

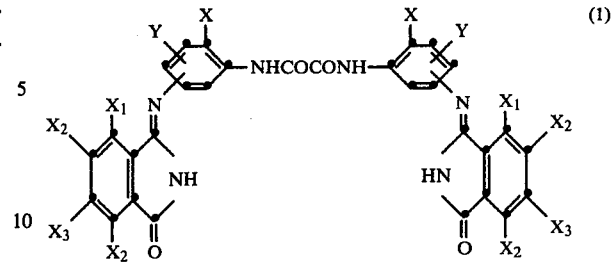

(1)

wherein X and Y are hydrogen, halogen, alkyl or alkoxy, each of 1 to 4 carbon atoms, $X_2$ is chlorine or bromine, and $X_1$ and $X_3$ are chlorine, bromine, alkoxy of 1 to 4 carbon atoms, or aryloxy.

2. An iminoisoindolinone pigment according to claim 1 of the formula

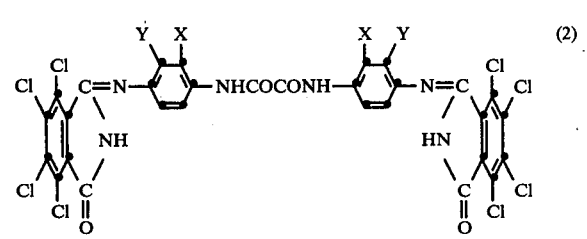

(2)

wherein X is hydrogen, chlorine, methyl or methoxy, and Y is hydrogen, methyl or chlorine.

3. An iminoisoindolinone pigment according to claim 2, wherein X is hydrogen, chlorine or methyl, and Y is hydrogen.

4. An iminoisoindolinone pigment according to claim 1 of the formula

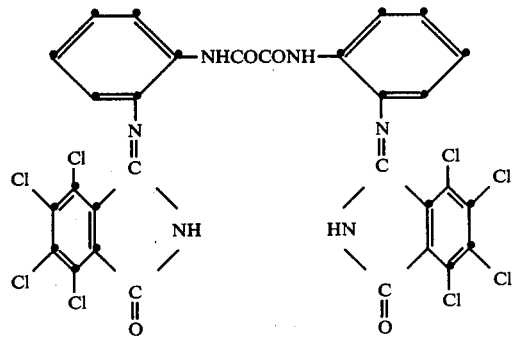

* * * * *